United States Patent [19]
de Laforcade

[11] 3,930,504
[45] Jan. 6, 1976

[54] PORTABLE LIGHT COAGULATOR

[75] Inventor: Hughes de Laforcade, Manchester, Mass.

[73] Assignee: Clinitex, Inc., Danvers, Mass.

[22] Filed: Dec. 21, 1973

[21] Appl. No.: 427,084

Related U.S. Application Data

[63] Continuation-in-part of Ser. No. 426,668, Dec. 12, 1973, abandoned, which is a continuation of Ser. No. 177,949, Sept. 7, 1971, abandoned.

[52] U.S. Cl. ............. 128/303.1; 350/206; 350/208; 350/212; 350/293
[51] Int. Cl.² .................... A61B 17/36; G02B 3/00
[58] Field of Search ............ 350/175 TS, 96 B, 212, 350/293, 206, 208; 351/1, 13, 14, 15, 16; 128/303.1, 395; 240/41.3

[56] References Cited
UNITED STATES PATENTS

| | | | |
|---|---|---|---|
| 3,084,694 | 4/1963 | Kavanagh et al. | 128/303.1 X |
| 3,164,058 | 1/1965 | Kosowsky | 240/41.3 X |
| 3,327,712 | 6/1967 | Kaufman et al. | 350/96 B X |
| 3,417,754 | 12/1968 | Smart | 351/13 X |
| 3,547,125 | 12/1970 | Tagnon | 351/1 X |
| 3,702,395 | 11/1972 | Rosendahl | 240/41.3 |
| 3,783,874 | 1/1974 | Koester et al. | 351/16 X |

*Primary Examiner*—Paul A. Sacher
*Attorney, Agent, or Firm*—Thomas C. Stover, Jr.

[57] ABSTRACT

A light coagulator for treatment of eye disorders is provided, utilizing a converging light beam, a collimated lens system and a mirror to deliver a high powered beam of light to the eye for use as a surgical tool. The light coagulator of the invention is of simplified design and portable.

11 Claims, 8 Drawing Figures

PORTABLE LIGHT COAGULATOR

The following is a continuation-in-part of applicant's co-pending continuation application Ser. No. 426,668 filed Dec. 12, 1973, which is a continuation of applicant's then co-pending application Ser. No. 177,949 filed Sept. 7, 1971 which co-pending applications are now abandoned.

FIELD OF THE INVENTION

This invention relates to a light coagulation system, particularly a light coagulating system for treatment of eye disorders.

THE PRIOR ART

Light coagulation, a method developed by medical and optical scientists for treating certain eye disorders, is gaining increasingly wide acceptance by the medical profession. In this treatment, an intense beam of light is focused on the eye, e.g. iris or retina, for a preselected time, to burn, weld, cauterize, i.e. coagulate the target area, usually a few milimeters in diameter. Through this method, various eye diseases, such as vascular diseases, retinal detachment, tumors, diabetic retinopathy and others can be treated without the need for conventional surgery.

Specifically, in diabetic retinopathy there is caused a proliferation of new blood vessels in the eye which lead to retina detachment and blindness. In diabetic retinopathy the blood vessels are cauterized by light coagulation before they overspread. Light coagulation treats this condition by cauterizing these vessels and checking the proliferation thereof.

In conventional light coagulation, a high intensity lamp, usually a Xenon arc lamp, is positioned in line with a series of lenses, e.g. five or more, called a condenser, which receives a portion of the light emitted and converts it to a beam which converges to a focal point and thereafter diverges.

Another lens, the objective, is positioned to receive the diverging beam and converts it to a parallel beam. The beam then passes to a mirror where it is reflected to the desired target area, e.g. the pupil of a patient's eye. The lens of the eye behind the pupil then focuses the entering beam to a point of convergence on the retina. The retina is thus treated, usually for a fraction of a second, then the light beam is cut off. The operator of the equipment, an M.D. eye specialist, observes and controls the treatment of the retina by observation through an aperture on the mirror. See, for example, FIG. 1 herein.

The above treatment, while successful, has in the past required a light coagulator that is both large and expensive. Some models are as wide as an office desk and higher and moveable only on wheels. Moreover, the lamps used in the light coagulators heretofore available have had high power requirements because, as indicated in FIG. 1, only a fraction of the light emitted is used, the remainder being wasted.

Because of their power requirements, size, and especially cost, light coagulators are usually found only in the larger hospitals. Often these hospitals are many miles from the patient and his doctor's office. The inconvenience and expense of transferring a patient to a remote hospital often leads to a delay in the patient receiving needed treatment.

A simplified light coagulator has heretofore not been available and there is a need and a market for a system that substantially overcomes these shortcomings. In particular, there is a need for a low cost light coagulator that is readily available in the office of the local opthamologist.

There has now been developed a light coagulator that is simpler in construction, portable, and considerably lower in cost than the above described system. At the same time, the light coagulator of the invention is at least as effective as its predecessors.

SUMMARY

Broadly, the present invention provides a light coagulator comprising a converging light beam source which directs high intensity light to a focal point and then diverges, an adjustable aperture diaphragm situated at said focal point for permitting adjustment of the size of the image field in the desired target area, a lens situated in the path of the diverging light beam for directing said diverging beam into a parallel light beam, means for directing said beam to a target area and means for observation of said target area.

By collimated optical system, as used herein, is meant an optical system that transforms a beam of light of a certain diameter or size to a parallel beam of another diameter or size.

DESCRIPTION

The invention will become more apparent from the following detailed description in which.

Figure 1:
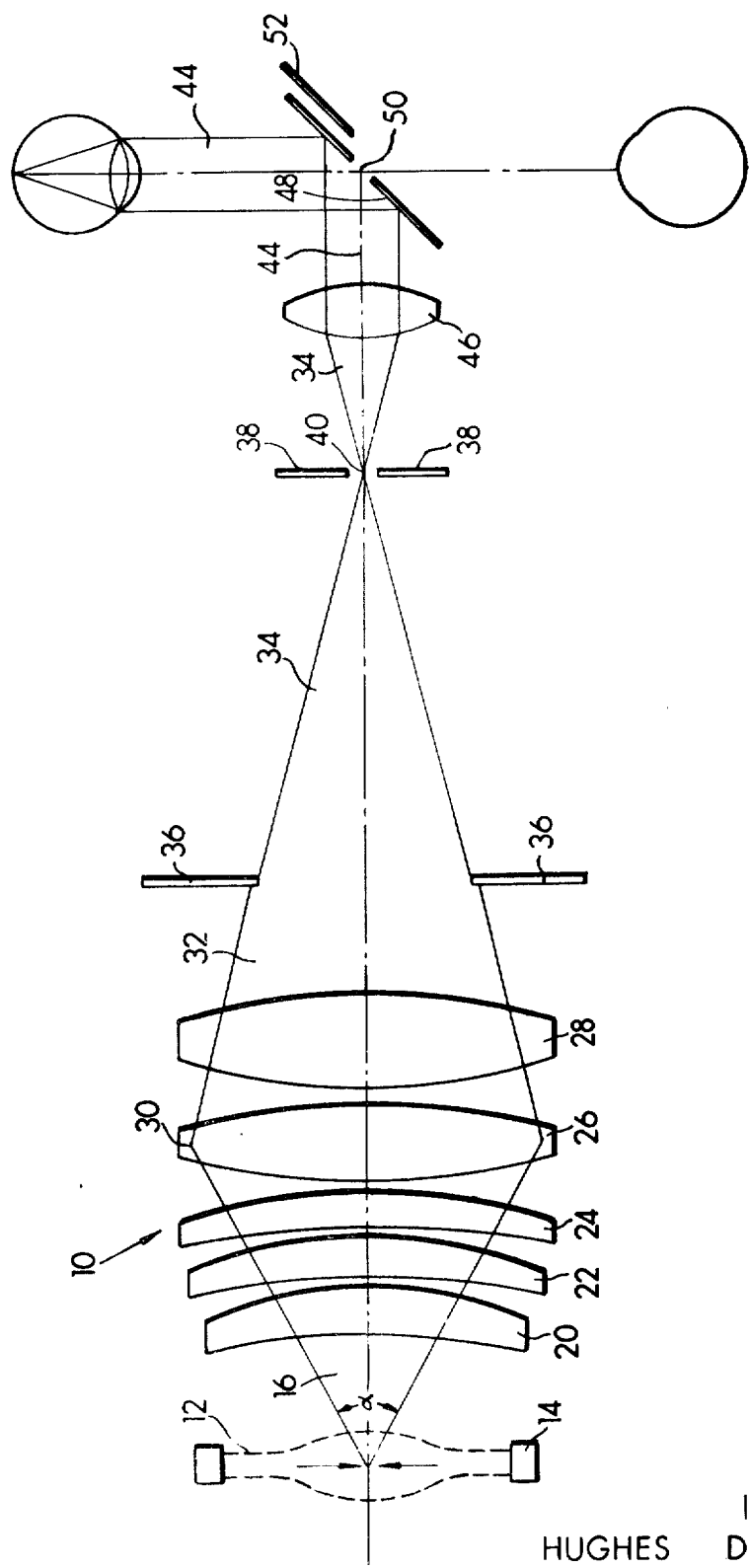
FIG. 1 is a schematic view of a light coagulating unit exemplifying the prior art.

Referring now to the drawings, light coagulator 10 has Xenon arc lamp 12 which emits light ray 16 through lenses 20, 22, 24, 26 and 28, i.e. the condenser, as shown in FIG. 1. At lens 26 at point 30 the ray 16 is converted to converging beam 32 which is reduced by pupil diaphragm 36 to convergent beam 34 which has focal point 40 as shown in FIG. 1. Situated at the focal point 40 is image field diaphragm 38 which permits adjustment of the size of the image field in the desired target area. From the focal point 40 the beam 34 inverts and diverges until contacting objective lens 46 which converts beam 34 to parallel beam 44 as illustrated in FIG. 1. Beam 44 is then reflected to a desired target area by rotatable mirror 48 which has aperture 50 therein for observation of the target area, e.g. the patient's retina, by the operator and a filter 52 which covers the aperture 48 and shields the operator's eye from the beam 44 as shown in FIG. 1. As further shown in FIG. 1, only a fraction of the emitted light is used by light coagulator 10, that light within the angle α.

Figure 2:
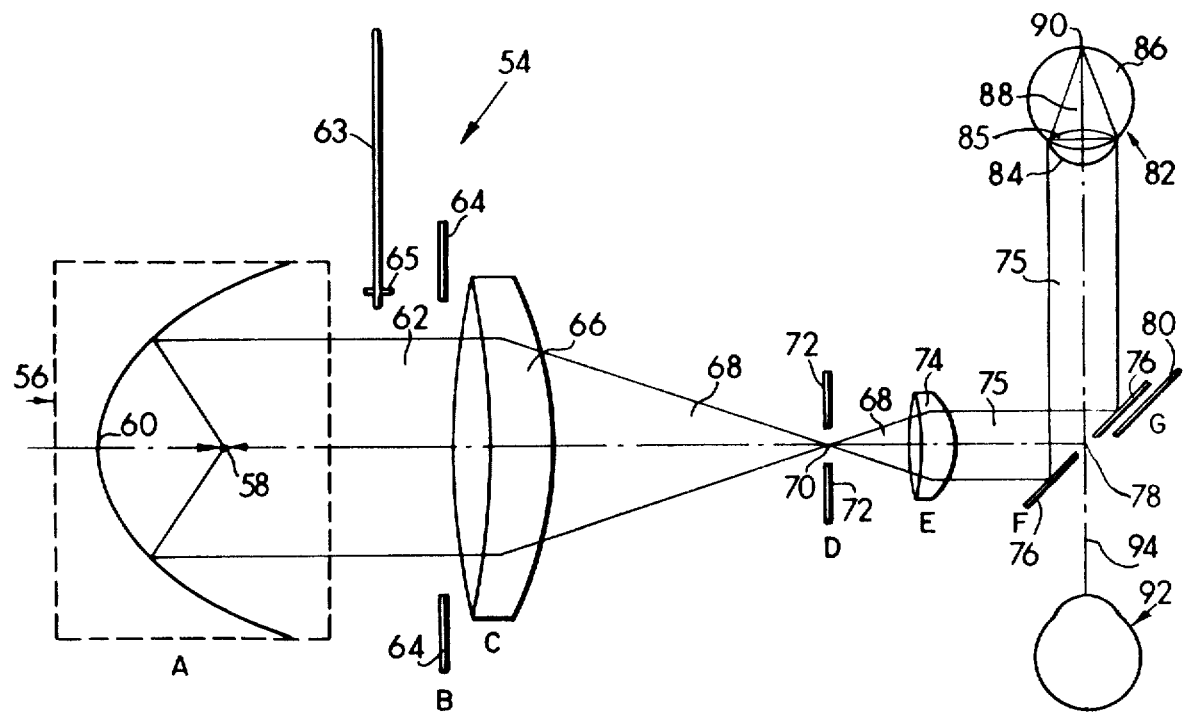
FIG. 2 is a schematic view of a light coagulating unit embodying the present invention.

In a considerably more compact unit, light coagulator 54 has lamp unit 56 which includes Xenon arc lamp 58 and paraboloid reflector 60 which is shaped to direct the major portion of the light emitted therefrom forward as parallel beam 62, as shown in FIG. 2. Beam 62 passes through pupil diaphragm 64 and lens 66 where beam 62 is converted to convergent beam 68 having focal point 70 which is surmounted by image field diaphragm 72 as shown in FIG. 2. At focal point 70, beam 68 inverts and diverges until it contacts objective lens 74 which converts beam 68 to parallel beam 75 as shown in FIG. 2. Parallel beam 75 is then reflected off rotatable mirror 76 to the desired target area, the patient's eye 82, having lens 85 and retina 86. The reflected beam 75 is converted by the lens 85 to convergent beam 88 which focuses to a small area or point 90 on retina 86. The retina 86 is treated by exposure for a fraction of a second to beam 88, which quickly heats and coagulates the area 90.

The treatment is observed and controlled by the operator who watches the treatment of the retina 86 through aperture 78 of mirror 76, filter 80 serving as a shield for the operator's eye 92 as shown in FIG. 2. Lenses 66, diaphragm 72 and lens 74 are referred to herein as the collimated system of the unit wherein the emitted light beam 62 is reduced in diameter and considerably intensified. The beam 75 is cut off by pivotably mounted shutter 63 which when activated quickly swings into position blocking light beam 62.

Figure 3:
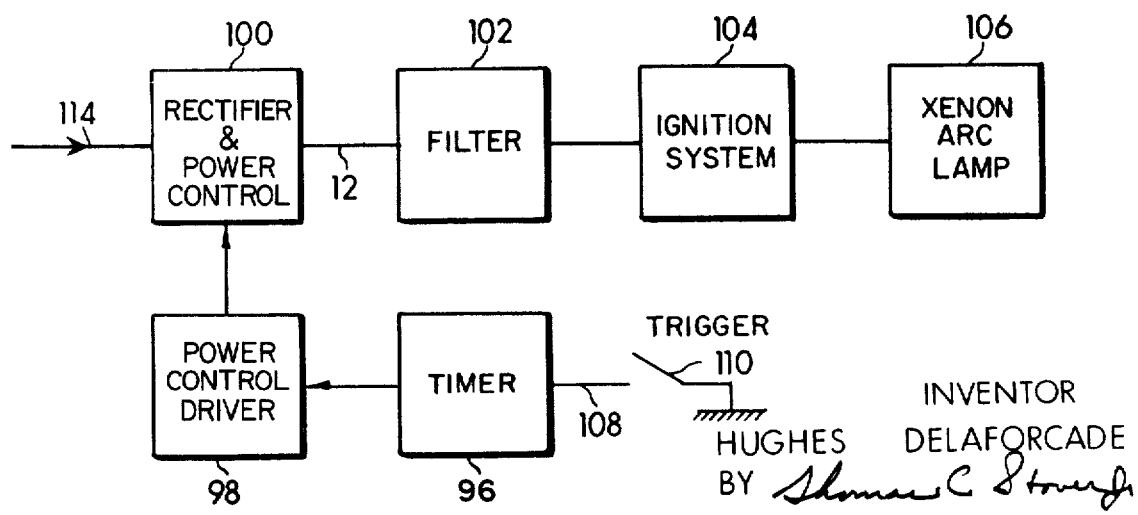
FIG. 3 is a block diagram of the power system suitable for powering the embodiment of FIG. 2.

Light coagulator 54 is powered as shown in FIG. 3, wherein the input voltage enters on line 114, is subject to rectification at rectifier and power control 100, then is passed to filter 102, ignition, system 104 and thence to the Xenon arc lamp 106. The circuit trigger 110 controls the timer 96 which is connected via power control driver 98 to rectifier and power control 100 as shown in FIG. 3. The intensity of the lamp 106 is controlled and adjusted by the power control 98 shown in FIG. 3.

Figure 4:
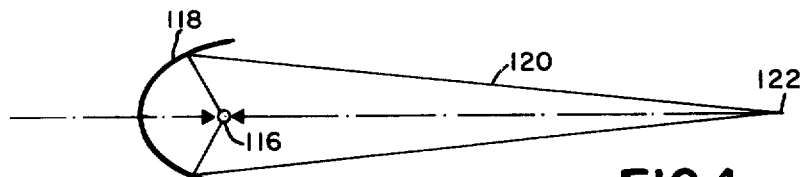
FIG. 4 is a schematic view of a portion of another embodiment of the light coagulating unit of the invention.

In addition to the paraboloid reflector described above, other rotationally symetric concave reflectors can be employed. Thus, in another embodiment of the invention, lamp 116 is backed by elipsoid reflector 118 which directs a light beam 120 to a focal point 122, without the need of an intervening lens, as shown in FIG. 4.

Figure 5:
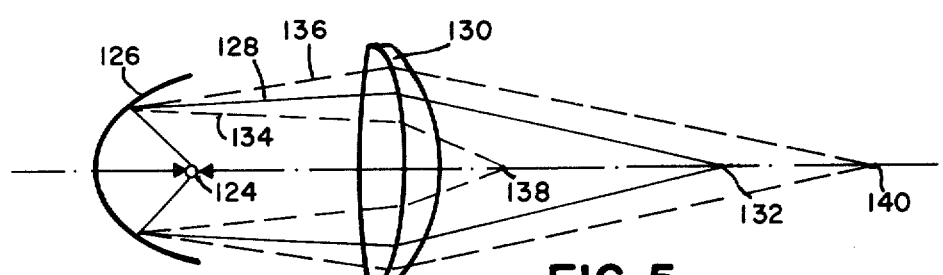
FIG. 5 is a schematic view of a portion of yet another embodiment of the light coagulating unit of the invention.

In a further embodiment of the invention, lamp 124 is backed by conoid reflector 126 which directs beam 128 through first lens 130 which focuses said beam to focal point 132 as shown in FIG. 5. Shown in phantom in FIG. 5 are other possible light beams 134 and 136 from said lamp reflector and lens to the prospective focal points 138 and 140. The inner beam 134, being already convergent, can, of course, dispense with the lens 130 if desired.

Figure 6:
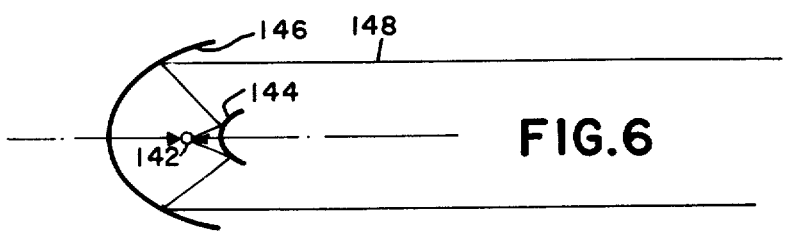
FIG. 6 is a schematic view of a portion of still another embodiment of the light coagulating unit of the invention.

In yet another embodiment of the invention, where the light beam is first expanded, then reduced, lamp 142 is fronted by convex reflector 144 which reflects the light back to rotationally symetric concave reflector 146 which directs the light beam 148 forward to lens and/or focal point (not shown) as shown in FIG. 6.

Figure 7:
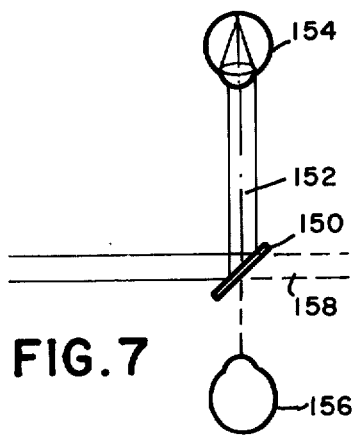
FIG. 7 is a schematic view of a beam splitter employed in the present invention.

In addition to apertured rotational mirror 76, other means can be employed to direct the intensified light beam to the target area, while permitting observation thereof. Thus, other rotational reflectors can be employed such as partially transparent beam splitter 150 which directs the greater portion of the collimated light beam 152 to the patient's eye 154, the operator 156 observing the treatment through the beam splitter 150 as shown in FIG. 7. A small portion 158 of the collimated light beam is lost through the beam splitter 150 as shown in FIG. 7.

Figure 8:
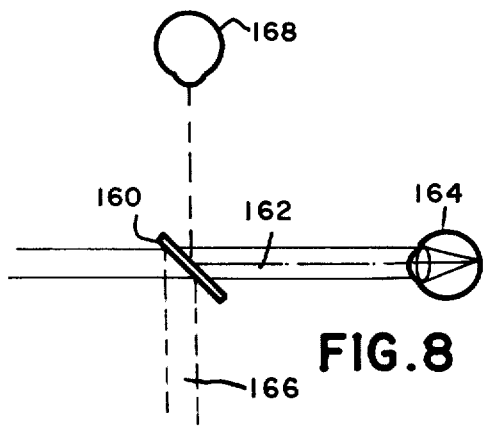
FIG. 8 is a schematic view of another beam splitter employed in the present invention.

In another embodiment partially transparent beam splitter 160 permits the greater portion of the collimated light 162 to pass therethrough to the patient's eye 164, the reflected portion of the beam 166 being lost, with the operator 168 observing the treatment as reflected off the beam splitter 160 as shown in FIG. 8.

From the above, it can readily be seen that the present invention provides a novel, efficient, simplified and compact light coagulating unit. More specifically, the invention provides a novel combination of a convergent light beam source, a collimated optical system and a rotatable mirror to direct the resultant light beam to the target area. The invention is particularly effective for treatment of eye disorders, e.g. iris, retina, by photo-coagulation of the treated area.

Although other types of lamps can be employed, e.g. the carbon-arc lamp, such lamp would be overly large and have undesirable spectrum characteristics compared to the Xenon arc lamps available. The Xenon arc lamps are of compact size and deliver a light beam of high intensity and have desirable spectrum characteristics, i.e. have a spectrum more closely approximating that of the sun. Accordingly, the Xenon arc lamp is preferred in the practice of the present invention.

As indicated above, various rotationally symetric concave reflectors backing the lamp can be employed within the present invention including conoid, elipsoid and paraboloid and optical deformations of conoid by means known in the art. A convex frontal reflector can be employed as shown in FIG. 6.

With certain conoid reflectors backing a lamp, e.g. elipsoid, a convergent beam is projected therefrom and the first lens is dispensed with. With other conoid reflectors backing a lamp, e.g. as shown in FIGS. 2 and 5, such first lens renders the beams convergent. Both types of lens systems are defined herein as a "convergent light beam source".

Of these reflectors preferred are the conoid shapes, particularly elipsoid and paraboloid. Particularly preferred is a Xenon arc lamp that emits a parallel beam of light. As indicated in FIG. 2, a lamp having a built-in paraboloid reflector emits such a parallel beam and utilizes about 80 percent of the light generated by the lamp. Alternatively, a paraboloid reflector can be separately added to a Xenon arc lamp or other high intensity lamp to provide a parallel beam of light within the scope of the present invention.

The addition of a concave reflector to a lamp, whether built-in or separate, permits the lamp to project a beam and utilizes for light coagulation more than 80 percent of the light generated by the lamp. Without such a reflector, only aobut 20 percent of the light generated is utilized for light coagulation. This is why, in the prior art, extra high powered lamps have been required to offset the considerable light losses inherent in the prior systems. Lamps of 1600 watts have been required, whereas the light coagulator of the present invention can employ a lamp of 150 watts or less, for a reduction ratio of more than 10 to 1.

Because of the reduction of the power requirement, the size and weight of the light coagulator of the present invention is reduced over the prior art by a factor of about 5 times.

Moreover, the light coagulator of the present invention can be plugged into the conventional 110 or 220 volt outlet, where the prior art instruments have required costly three-phase electrical installation in addition to its high purchase price.

The purchase price of the light coagulation of the present invention is reduced over the prior art by a factor of 3 to 5 times. Accordingly, the light coagulator of the invention is accessible to widespread distribution in local opthamologists' offices allowing for greater number of patients to be treated earlier for eye disorders.

The lamp employed can have any power rating sufficient to provide a beam of the desired intensity. A suitable Xenon arc lamp employed in the present invention is one rated at 150 watts or less, up to 500 watts or more.

A suitable first lens for the present invention, where required, is a lens which can direct a beam of light to a focal point or near focal point (focal zone). Preferred is a lens which can bend a beam of light to a focal point or near point. Particularly preferred is a lens that can bend a beam of light to a focal point or zone including the rays at the infrared end of the spectrum, i.e. a lens that can correct up to the infrared rays, e.g. the coated achromat lens, which corrects for various wavelengths so as to focus all colors at the same point or zone, including the infrared (up to 1000 nanometers).

The objective lens, that lens situated beyond the above described focal point, is a lens similar to the first, specifically it is a coated achromat lens. It is preferably positioned so that its focal point coincides with that of the first lens and it is structured to convert the rays diverging from the focal point into the resultant parallel beam of light.

In sum, both lenses are coated to minimize spherical aberrations and achromatic to correct for chromatic aberrations as discussed above.

The diaphragms are standard available diaphragms in the optical field having adjustable apertures therein to regulate the light beam sizes as discussed above. The first diaphragm adjusts the beam size reaching the patient's pupil. The recommended maximum beam diameter is 8.5 mm to fit safely inside a fully dilated pupil.

The second diaphragm is positioned at the lenses' focal point and by adjustment of the aperture thereof, one can adjust the size of the treated area on the patient's retina at angles, for example of 2° through 3°, 4.5° and 6°. This angle is measured at the nodal point of the eye.

The resultant light beam is aimed to the target area directly as shown in FIG. 8 or by a rotational reflector including a mirror or partially transparent beam splitter as described above. The beam splitter can be constructed of plastic (mylar), glass and preferably coated glass. The rotatable mirror can be constructed of various reflective materials including glass and is preferably constructed of 100 percent high reflectance aluminum for high reflective efficiency.

In the mirror, usually at the center thereof, is a small aperture, about 2 mm, to permit the operator, e.g. an M.D. eye specialist, to observe and control the treatment of the retina.

The filter is adapted to be positioned over the observation aperture to protect the observor's eye. The filter can be of tinted glass or plastic, and preferably is of black glass. The preferred rotational reflector is an apertured aluminum mirror.

As indicated in FIG. 3, an automatic timer controls the length of treatment of the beam on the retina. Recommended for most treatments are times of 0.5 seconds or less. However, greater time periods up to 3.0 seconds or more can be employed where desired.

The following example is presented to illustrate the invention and should not be construed in limitation thereof.

EXAMPLE I

Portable light coagulators according to the present invention have been built, tested and used by opthamologists in their offices. The units weigh only about 50 lbs., operate off the readily available 110 v/220v systems, and require only a 150 watt Xenon arc lamp. These lamps have successfully treated eye disorders, including diabetic retinopathy, tumors and have successfully welded detached retinas back to the choriod of the eye.

What is claimed is:

1. A light coagulator comprising in combination an arc-lamp parallel light beam source, a first lens for focusing at least a portion of the light into a beam of light converging toward a focal point and then diverging, an adjustable aperture diaphragm situated at said focal point for permitting adjustment of the size of the image field in the desired target area, a second lens situated in the path of the diverging light beam for directing said diverging beam into a parallel light beam and a rotatable mirror positioned in the path of said parallel beam, for reflecting said beam to a target area, said mirror having an aperture therethrough for observation of the target area wherein said light source is a lamp backed by a rotationally symetric concave reflector which directs the light forward in a parallel beam toward said first lens, and wherein an aperture diaphragm is positioned between said light source and said first lens to control the size of the light passing through siad first and second lenses.

2. The apparatus of claim 1 wherein said rotationally symetric concave reflector is a paraboloid reflector.

3. The system of claim 1 wherein said light source is a Xenon arc lamp at a rated power of at least 150 watts backed by a paraboloid reflector.

4. The apparatus of claim 1 wherein said focal point is situated between said first and second lenses, the lenses being situated so that their focal points coincide.

5. The apparatus of claim 1 wherein said mirror is situated to direct said parallel light beam to a portion of an eye.

6. The aperture of claim 1 wherein said mirror has an observation aperture therethrough and a light filter positionable over said aperture to protect the eye of the observer.

7. The apparatus of claim 1 wherein said aperture diaphram is an adjustable aperture diaphragm.

8. The apparatus of claim 1 wherein said second lens is of smaller radius of curvature than said first lens to form a resultant parallel light beam that is increased in intensity and reduced in diameter to pass through the pupil of the eye.

9. The apparatus of claim 1 wherein means are provided to adjust the light output intensity of said light source and said light source has a shutter to cut off said light beam.

10. The apparatus of claim 1 wherein said focal point is situated between said first and second lenses, said mirror has an observation aperture therethrough, a first light diaphragm is positioned between said light source and said first lens and a second light diaphragm is positioned proximate said focal point.

11. The apparatus of claim 1 wherein said first and second lenses are coated achromat lenses and said apparatus is portable.

* * * * *